United States Patent [19]

Barner et al.

[11] Patent Number: 4,958,035

[45] Date of Patent: Sep. 18, 1990

[54] PROCESS FOR SYNTHESIZING CHROMANES

[75] Inventors: Richard Barner, Witterswil; Josef Hübscher, Nunningen, both of Switzerland

[73] Assignee: Hoffmann-La Roche Inc., Nutley, N.Y.

[21] Appl. No.: 373,000

[22] Filed: Jun. 29, 1989

Related U.S. Application Data

[62] Division of Ser. No. 235,257, Aug. 23, 1988, Pat. No. 4,876,369.

[30] Foreign Application Priority Data

Aug. 25, 1987 [CH] Switzerland ............... 3244/87

[51] Int. Cl.$^5$ ............................................ C07D 311/70
[52] U.S. Cl. .............................................. 549/408
[58] Field of Search ............................... 549/408

[56] References Cited

FOREIGN PATENT DOCUMENTS 0058945  9/1982  European Pat. Off. .

OTHER PUBLICATIONS

Kitamura, J. Am Chem Soc. 108, 6071–6072, (1986).
Houben–Weyl, Meth. Der Organ. Chemie, Bd. XIII/2a, pp. 592–601.
Gray, J. Org. Chem. 49, 2288 (1984).
Barner, Helv, Chemica Acta 62, Fasc. 7 (1979).
L. J. Smith, Am. Chem. Soc. 59, 673 (1937).
McCormick et al., Methods in Enzymology, vol. VIII, Vitamins and Coeyzymes Park C. (1971). pp. 272–273.

*Primary Examiner*—Nicky Chan
*Attorney, Agent, or Firm*—George M. Gould; Bernard S. Leon; William H. Epstein

[57] ABSTRACT

The present invention is directed to a novel process for producing chromane derivatives, which are suitable as intermediates for the manufacture of d-α-tocopherol (natural vitamin E), and with a process for producing d-α-tocopherol itself.

2 Claims, No Drawings

PROCESS FOR SYNTHESIZING CHROMANES

This is a division, of application Ser. No. 07/235,257 filed Aug. 23, 1988, now U.S. Pat. No. 4,876,369.

SUMMARY OF INVENTION

The present invention is concerned with a novel process for the manufacture of chromane derivatives, which are suitable as intermediates for the manufacture of d-α-tocopherol (natural vitamin E), and with a process for the manufacture of d-α-tocopherol itself. Furthermore, the invention is concerned with novel intermediates in this process.

Several processes for the manufacture of natural vitamin E are already known, but they are only of limited interest from the industrial point of view. Accordingly, natural vitamin E has hitherto been extracted almost exclusively from natural sources.

There accordingly exists a need for a technically realizable process in accordance with which natural vitamin E can be obtained in good yield and with high optical purity. This is now made possible by means of the process in accordance with the invention.

DETAILED DESCRIPTION

This Process comprises reacting phytenal. i.e. the compound of the formula

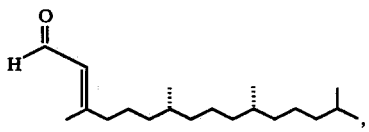

I with a compound of the formula

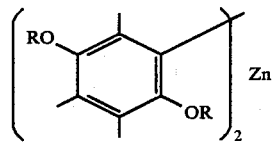

II wherein OR is a hydrolyzable ether group, using a chiral catalyst of the formula

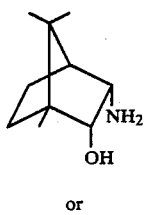

III or

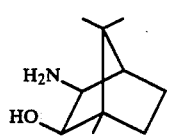

IV if desired, converting a thus-obtained compound of the formula

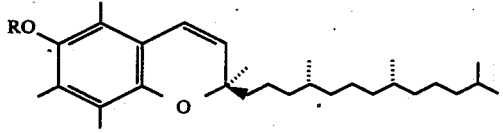

wherein OR is as above, into d-α-tocopherol.

The residue —OR signifies in the scope of the present invention a group which is cleavable by hydrolysis to form OH. R can be any conventional ether protecting group which upon hydrolysis is cleared to regenerate the hydroxy group which X protects. R is preferably silyl or alkoxymethyl, for example methoxymethyl, or also tetrahydropyranyl. Furthermore, the notation " " signifies that the corresponding residue is situated above the plane of the molecule, while the notation " " signifies that the corresponding residue is situated below the plane of the molecule.

The reaction of phytenal with a compound of general formula II is conveniently effected by firstly preparing a compound of formula II in solution in accordance with the following reaction sequence:

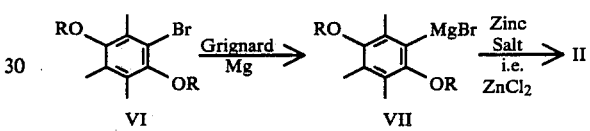

in a manner known per se (see e.g. L. I. Smith et al., J. Amer. Chem. Soc. 59, 673 (1937), R. Barner et al., Helv. 62, 2384 (1979), R. A. Grey, J. Org. Chem. 49, 2288 (1984), Houben-Weyl, Methoden der organischen Chemie, 2nd Ed. (1924), Vol. 4, 754 et seq.). Thereupon, the compound III or IV is added.

In carrying out this reaction the compound of formula III or compound of formula IV can be used in catalytic quantities. However, larger quantities of the compound of either formula III or formula IV can be used. Generally it is preferred to utilize about 2 mole % of the compound of formula III or IV based upon the moles of the compound of formula II in the reaction medium. In carrying out the reaction to produce the compound of formula V any convenient mole ratio at the compounds of formula I and II can be utilized with the preferred mole ratio being about 1 to 1. In carrying out this reaction temperature and pressure are not critical and room temperature and atmospheric pressure can be utilized. If desired elevated or reduced temperatures may be utilized.

The compound of formula I is suitably added to the reaction medium containing the compound of formula II and the chiral catalyst of formula III or IV. Any conventional inert organic solvent can be used as the reaction medium. Among the preferred inert organic solvents are those conventionally used in the metalorganic reactions. Examples of such solvents are ethers, especially cyclic ethers such as tetrahydrofuran or dioxan, or mixtures of these ethers with aliphatic or aromatic hydrocarbons such as, especially, pentane, hexane, benzene, toluene and the like.

The catalyst III or IV can be used as such or in polymer-bound form.

The compounds of formula V are novel and are likewise an object of the present invention. The conversion of such a compound into d-α-tocopherol by hydrogenation of the double bond and cleavage of the protecting group can be effected in a manner known per se; the hydrogenation e.g. catalytically with hydrogen or by means of alkali metal/C₂H₅OH and the removal of the protecting group by acidic hydrolysis or solvolysis.

The catalytic hydrogenation is conveniently effected in the presence of a mineral acid (simultaneous cleavage of the protecting group). The especially suitable catalyst is Pt or Pd.

The reduction by means of an alkali metal, especially by means of sodium, in ethanol is conveniently effected at an elevated temperature, especially at the reflux temperature; see also Methods in Enzymology, Vol. XVIII, Vitamins and Coenzymes, Part C, D. B. McCormick and L. D. Wright, Academic Press N.Y., 1971, page 272.

The following Example illustrates the invention, but does not represent any limitation thereof.

EXAMPLE 1.6 g (5 mmol) of bromotrimethyldimethoxybenzene was converted into the Grignard reagent in a known manner with magnesium in dry tetrahydrofuran and the zinc derivative is obtained by adding 240 mg (2.5 mmol) of zinc chloride, which requires 30 minutes. Toluene was added and 15 mg (0.09 mmol) of endo-aminoborneol are added at room temperature. Subsequently, 1.2 g (4.1 mmol) of (7R,11R)-E-3,7,11,15-tetramethyl-hexadec-2-en-1-al were added and, after stirring for 16 hours, the mixture was hydrolyzed with aqueous ammonium chloride solution. The mixture was extracted with ethyl acetate and the extracts were dried and concentrated. The resulting dehydrotocopherol methoxymethyl ether was hydrogenated in MeOH/1% HCl over PdC (5%) (simultaneous removal of the protecting group). It was concentrated and subsequently chromatographed on silica gel with toluene. There is obtained 0.37 g (55% yield) of d-α-tocopherol. The optical purity was determined by gas-chromatographical analysis of the methyl ether.

We claim:
1. Compound of the formula

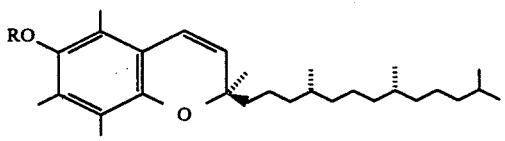

wherein OR is a hydrolyzable ether group.
2. The compound of claim 1, wherein said compound is 3,4-dehydro-(2R,4′R,8′R)-α-tocopheryl methoxymethyl ether.

* * * * *